US010357047B2

(12) United States Patent
Pujol et al.

(10) Patent No.: US 10,357,047 B2
(45) Date of Patent: Jul. 23, 2019

(54) ***ARTHROBACTER GANDAVENSIS* STRAINS**

(71) Applicant: ADISSEO FRANCE S.A.S., Antony (FR)

(72) Inventors: Ange Pujol, Saint Savournin (FR); Michel Fons, Aix en Provence (FR); Caroline Mirande, Ambérieu en Bugey (FR); Estelle Devillard, Montluçon (FR); Lamya Rhayat, Sauvagny (FR)

(73) Assignee: ADISSEO FRANCE S.A.S., Antony (FR)

( * ) Notice: Subject to any disclaimer, the term of this patent is extended or adjusted under 35 U.S.C. 154(b) by 0 days.

(21) Appl. No.: 15/317,384

(22) PCT Filed: Jun. 17, 2015

(86) PCT No.: PCT/FR2015/051611
§ 371 (c)(1),
(2) Date: Dec. 8, 2016

(87) PCT Pub. No.: WO2015/193618
PCT Pub. Date: Dec. 23, 2015

(65) Prior Publication Data
US 2017/0099858 A1 Apr. 13, 2017

(30) Foreign Application Priority Data

Jun. 17, 2014 (FR) ..................................... 14 55536

(51) Int. Cl.

| | |
|---|---|
| *A23K 10/18* | (2016.01) |
| *C12R 1/06* | (2006.01) |
| *A61K 35/74* | (2015.01) |
| *C07K 14/305* | (2006.01) |
| *A23L 33/135* | (2016.01) |
| *A23L 33/18* | (2016.01) |
| *A23K 20/147* | (2016.01) |

(52) U.S. Cl.
CPC ............ *A23K 10/18* (2016.05); *A23K 20/147* (2016.05); *A23L 33/135* (2016.08); *A23L 33/18* (2016.08); *A61K 35/74* (2013.01); *C07K 14/305* (2013.01); *C12R 1/06* (2013.01)

(58) Field of Classification Search
None
See application file for complete search history.

(56) References Cited

U.S. PATENT DOCUMENTS

2012/0263688 A1 10/2012 Crost et al.

FOREIGN PATENT DOCUMENTS

| | | | |
|---|---|---|---|
| KR | 2008 0075389 | A | 8/2008 |
| WO | 2006/104388 | A2 | 10/2006 |
| WO | 2008/152252 | A2 | 12/2008 |

OTHER PUBLICATIONS

Storms et al., International Journal of Systematic and Evolutionary Microbiology, vol. 53, pp. 1881-1884, 2003.*
Sep. 11, 2015 Search Report issued in International Patent Application No. PCT/FR2015/051611.
Hammami, Riadh et al., "Anti-infective properties of bacteriocins: an update", Cellular and Molecular Life Sciences, Aug. 2013, vol. 70, No. 16, XP 055116653, pp. 2947-2967.
Wietz, Matthias et al., "Wide Distribution of Closely Related, Antibiotic-Producing Arthrobacter Strains throughout the Arctic Ocean", Applied and Environmental Microbiology, Mar. 15, 2012, vol. 78, No. 6, XP 055096498, pp. 2039-2042.
Kamigiri, K. et al., "YM-30059, a Novel Quinolone Antibiotic Produced by *Arthrobacter* sp.", Journal of Antibiotics, Japan Antibiotics Research Association, Aug. 1996, vol. 49, No. 8, XP 000974176, pp. 823-825.

* cited by examiner

*Primary Examiner* — Richard G Hutson
(74) *Attorney, Agent, or Firm* — Oliff PLC

(57) ABSTRACT

An *Arthrobacter gandavensis* strain having an activity against *Clostridium perfringens* selected from the strains AP1 filed with DSMZ on Feb. 19, 2014 under the number DSM 28444, AP2 filed with DSMZ on Feb. 19, 2014 under the number DSM 28445, AP3 filed with DSMZ on Feb. 19, 2014 under the number DSM 28446 or AP4 filed with DSMZ on Feb. 19, 2014 under the number DSM 28447.

9 Claims, 7 Drawing Sheets

Specification includes a Sequence Listing.

ARTHROBACTER GANDAVENSIS STRAINS

The present invention relates to new bacterial strains having an interest as a probiotic in animal feed and more particularly for chicken feed.

Some bacterial strains have the ability to release substances having a bacteriostatic or bactericidal effect on their competitors. These antimicrobial substances can be of organic nature, for example organic acids or hydrogen peroxide (Ross et al., Int. J. Food Microbiol. 79, 3-16, 2002) or of peptide nature. Furthermore, the enzymatically synthesized antimicrobial peptides which belong to the class of antibiotics (Mootz et al., Curr. Opin. Chem. Biol. 1, 543-551, 1997; Keating et al., Curr. Opin. Chem. Biol. 3, 598-606, 1999), and the peptides produced by the ribosomal route which form the class of the class of bacteriocins (Jacob et al., Ann. Inst. Pasteur (Paris) 84, 222-224, 1953) are distinguished.

The bacteriocins arouse a growing interest in the world of research and industry; they might provide alternative solutions to the use of antibiotics, in particular in animal husbandry (Luchansky, Antonie Van Leeuwenhoek 76, 335, 1999; O'Sullivan et al., Biochemistry 84, 593-604. 2002).

Many heterologous expression systems of these bacteriocins are developed over the past few years. In particular, Morisset et al. (Morisset et al., Appl. Environ. Microbiol., 70, 4672-4680, 2004) have produced variants mésentricine Y105, bacteriocin of class IIa produced by *Leuconostoc mesenteroides* subsp. *mesenteroides* Y105, in *Leuconostoc mesenteroides* subsp. *dextranicum* DSM20484. Similarly, Flynn et al. (Microbiol., 148, 973-984, 2002) conducted the expression of the gene ABP-118, bacteriocin of class IIb originally produced by *Lactobacillus salivarius* subsp. *salivarius* UCC118, in the hosts *Lactobacillus plantarum*, *Lactococcus lactis* and *Bacillus cereus*.

Furthermore, several assays were conducted to express the genes of the bacteriocins in the bacterium *Escherichia coli* (McCormick et al., Appl. Environ. Microbiol., 64, 4757-4766, 1998; Garneau et al., Appl. Environ. Microbiol., 69, 1352-1358, 2003; Biet et al., Microbiol., 144, 2845-2854, 1998; Miller et al., Appl. Environ. Microbiol., 64, 14-20, 1998; Richard et al., J. Bacteriol., 186, 4276-4284, 2004; Kloche et al., Appl. Microbiol. Biotechnol., 67:532-538, 2005), the yeast *Saccharomyces cerevisiae* (Schoeman et al., Yeast, 15, 647-656, 1999; Van Reenen et al., Int. J. Food Microbiol., 81, 29-40, 2003) and in lactic acid bacteria (Rodriguez et al., Int. J. Food Microbiol., 80, 101-116, 2003).

Several works are therefore carried out in order to identify new bacteriocins and new bacterial strains to produce bacteriocins.

The digestive ecosystem consists of an abundant and very complex microbiota grouping bacteria, yeasts and Archaea. This microbiota is essentially anaerobic and bacteria of the genera *Bacteroides, Eubacterium, Clostridium, Ruminococcus, Bifidobacterium* and *Fusobacterium* (Suau et al., Appl. Environ. Microbiol. 65, 4799-4807, 1999) are mainly found. The microbiota has an important impact on the health of the host. It is in particular involved in the toxification and the detoxification of metabolic compounds coming from food (Hughes and Rowland, Microbial Ecology Health Disease 2, 179-185, 2000). It is also capable of modulating the expression of enterocytic functions (Bry et al., Science 273, 1380-1383. 1996; Hooper et al., Science 291, 881-884. 2001). Finally, it plays a vital role in protecting the host against the invasion by potentially pathogenic exogenous bacteria (Ducluzeau et al., Microbial Ecology and Intestinal Infections, 1988. Fons et al., Microbial Ecology in Health and Disease 2, 240-246, 2000).

Among the known intestinal pathogens, there is *Clostridium perfringens*, Gram-positive, strictly anaerobic bacterium able to sporulate and widespread in the environment. This pathogen can come from food, but can also be present in low concentration in the intestine and begin to proliferate and secrete toxins under the effect of stress. The *Clostridium perfringens* strains are classified into 5 toxinotypes according to the toxins they produce (Petit et al., Trends Microbiol. 7, 104-110, 1999). The strains of *C. perfringens* type A are responsible for gastro-intestinal diseases in humans. In 1997, over 245,000 cases of *C. perfringens* infections have been reported in the United States. This led to the hospitalization of 41 people including 7 who did not survive (Mead et al., Emerg. Infect. Dis. 5, 607-625, 1999). The strains of *C. perfringens* type A and C can be respectively the origin of necrotic enteritis in poultry and pigs. In poultry, the necrotic enteritis is a rapidly evolving acute pathology, the mortality of which can reach 1 to 2% per day. Besides its impact on the welfare of animals, therefore this pathology can have a significant economic impact. Until 1999, this disease was well controlled by the use of antibiotics as growth factors. But in 1999, the European Union prohibited their use partially, then completely in 2006 in the animal feed for fear of selecting the resistant bacteria and therefore seeing the effectiveness of antibiotics decrease in humans. Since this prohibition, the necrotic enteritis caused by *Clostridium perfringens* in poultry and pig is no longer controlled in Europe. The number of cases reported to the National Network of Epidemiological Observations in Poultry farming (RNOEA) (AFSSA Ploufragan) significantly increased in 1999 and 2000 (Valancony, Bulletin of GTV 12, 9-12, 2001).

Dabard et al. (Appl. Environ. Microbiol., 67, 4111-4118, 2001) showed that the strain *Ruminococcus gnavus* E1, isolated from the dominant flora in Human, is capable of producing an antimicrobial substance, called ruminococcin A or RumaA, which accumulates in the culture supernatant. It is about a bacteriocin belonging to the family of lantibiotics, active against various pathogenic strains of *Clostridium* sp. *Ruminococcus gnavus* is a strictly anaerobic bacterium belonging to the family of Lachnospiraceae, in the Clostridiales order.

The patent application WO 2008/152252 relates to a bacterial strain of *Ruminococcus gnavus* (filed with the CNCM under the number I-3705 as well as the peptides RumC1, RumC2 and RumC3 having an antibacterial activity against *Clostridium perfringens*, as well as the genes encoding for these peptides.

To date, the research for alternative solutions in order to control and treat the diseases associated with the *Clostridium perfringens* proliferation is therefore of major importance.

The present invention surprisingly allowed to identify new *Arthrobacter gandavensis* strains synthesizing peptides having antibacterial activity (as bacteriocins) against *Clostridium perfringens*.

DESCRIPTION OF THE INVENTION

The present invention relates to a strain of *Arthrobacter gandavensis*, having activity against *Clostridium perfringens* selected from *Arthrobacter gandavensis* AP1 filed on Feb. 19, 2014 with DSMZ under the number DSM 28444, *Arthrobacter gandavensis* AP2 filed on Feb. 19, 2014 with DSMZ under the number DSM 28445, *Arthrobacter gan-*

*davensis* AP3 filed on Feb. 19, 2014 with DSMZ under the number DSM 28446, or *Arthrobacter gandavensis* AP4 filed on Feb. 19, 2014 with DSMZ under the number DSM 28447.

In the context of the present invention, the activity against *Clostridium perfringens* can be defined as the ability to inhibit the growth or the development of target bacteria or the ability to kill target bacteria. The measurement techniques of the antimicrobial activity are known to those skilled in the art. The activity against *Clostridium perfringens* can be defined by an activity test as described in the point 4.3 of the example 4 hereinafter or in the patent application WO2008/152252 (and more particularly at page 23 & 24: «2. Test of antimicrobial activity from a liquid sample» or page 24: «3. Test of antimicrobial activity from colonies growing in agar medium»: The antimicrobial activity in this case is highlighted in the present invention by an inhibition test of the *Clostridium perfringens* CpA strain cultured on agar medium. The sample containing one of the peptides of the invention is deposited in wells formed in the agar medium. The antimicrobial activity is highlighted when an inhibition halo is formed around the well.

The invention also relates to a compound having an activity against *C. perfringens* isolated from a bacterial strain selected from *Arthrobacter gandavensis* AP1 filed on Feb. 19, 2014 with DSMZ under the number DSM 28444, *Arthrobacter gandavensis* AP2 filed on Feb. 19, 2014 with DSMZ under the number DSM 28445, *Arthrobacter gandavensis* AP3 filed on Feb. 19, 2014 with DSMZ under the number DSM 28446, *Arthrobacter gandavensis* AP4 filed on Feb. 19, 2014 with DSMZ under the number DSM 28447.

In a particular embodiment of the invention, the peptide has a sequence selected from SEQ ID No. 1 to SEQ ID No. 16.

The invention also relates to biologically active fragments of these peptides having an antimicrobial activity. The term «biologically active fragments» of a peptide refers to a peptide comprising a part but not the totality of the peptide from which it is derived and which have kept the antimicrobial activity of the polypeptide from which it is derived.

The preparation methods of the peptides of sequences SEQ ID No. 1 to SEQ ID No. 16 are known to those skilled in the art.

The sequences of these peptides have high identities with the peptides RumC of the strain *Ruminococcus gnavus* filed with the CNCM under the number 1-3705. The methods for measuring and identifying the degree of identity and the degree of similarity between polypeptides are known to those skilled in the art. The alignment of the sequences is for example made by means of Vector NTi 9.1.0, alignment program AlignX (Clustal W algorithm) (Invitrogen INFORMAX, http://www.invitrogen.com) or using the tool CLUSTAW (http://www.ebi.ac.uk/clustalw/).

The peptides of the invention are secreted (or released) by the bacteria in the extracellular environment. It is possible that any one of the peptides of sequences SEQ ID No. 1 to SEQ ID No. 16 comprises a signal peptide of a determined number of amino acids. In this case, the invention also concerns the mature peptide obtained after cleavage of the signal peptide.

In another embodiment, the potential signal peptide of the peptide SEQ ID No. 1 to SEQ ID No. 16 can be replaced by a heterologous signal peptide in order to make the expression and the secretion of this peptide by a heterologous host organism.

The peptides according to the invention may be isolated or purified from their natural environment. They may in particular be isolated from cecal and ileal microbiota of animals and in particular of pigs hosting the *Arthrobacter gandavensis* strain. The peptides can be prepared by means of different processes. These processes are in particular the purification from natural sources such as bacteria naturally expressing these peptides, the production of recombinant peptides by appropriate host cells and subsequent purification thereof, the production by chemical synthesis or, finally, a combination of these different approaches. Thus, the peptides of the sequences SEQ ID No. 1 to 16 of the present invention may be isolated from one of the strains of *Arthrobacter gandavensis* AP1 filed with DSMZ under the number DSM 28444, *Arthrobacter gandavensis* AP2 filed with DSMZ under the number DSM 28445, *Arthrobacter gandavensis* AP3 filed with DSMZ under the number DSM 28446, or *Arthrobacter* or *gandavensis* AP4 filed with DSMZ under the number DSM 28447.

In another embodiment, the peptides of the present invention are isolated from recombinant host organisms expressing a compound according to the invention or a fragment of a compound having an antimicrobial activity.

The invention also relates to fusion proteins, recombinant proteins or chimeric proteins comprising the peptides according to the invention.

According to one embodiment of the present invention, the peptide is adapted for a use in nutrition or in pharmacy, for example for a use in animal nutrition.

The term «peptide adapted for use in nutrition or pharmacy» means a peptide whose characteristics are such that it is suitable for nutrition or pharmacy. The essential characteristics for a use in nutrition or pharmacy are in particular the pH at which the peptide can resist, the resistance to the gastric enzymes and the preservation of their activity at physiological temperatures. Indeed, part of the digestive system of animals and Humans is acid and it is therefore essential that the peptide is resistant to this pH. Another characteristic essential for a use in nutrition is the temperature at which the antimicrobial substance is active. Indeed, the forming of the antimicrobial substance in a drug, a nutritional additive or an animal feed, for example, involves treatments and a temperature greater than the ambient temperature. The activity of the used antimicrobials must therefore be stable under the conditions of the processes, in particular the conditions of temperatures. The antimicrobials used must also be active at physiological temperatures (37-41° C.).

According to one embodiment of the present invention, the peptide or a mixture of peptides according to the invention presents an antimicrobial activity at neutral pH and retains its antimicrobial activity at an acidic pH, for example lower than 7, preferably lower than 4.4 and in particular at pH2.

According to one embodiment of the present invention, the peptide or a mixture of peptides according to the invention presents an antimicrobial activity at 37° C. and retains this activity at temperatures lower than and greater than the ambient temperature, for example greater than 50° C.

The present invention also relates to a polynucleotide encoding for a peptide having an activity against *Clostridium perfringens* selected from polynucleotides whose sequence is defined by SEQ ID No. 17 to SEQ ID No. 32, the polynucleotides which hybridize to the polynucleotide according to any one of the sequences SEQ ID No. 17 to SEQ ID No. 32, or the polynucleotides encoding for a peptide as defined hereinabove.

According to the present invention, the term «polynucleotide» means a single-stranded nucleotide chain or its complementary which can be of DNA or RNA type, or a double-stranded nucleotide chain which can be of complementary or genomic DNA type. Preferably, the polynucleotides of the invention are of the DNA type, in particular double-stranded DNA. The term «polynucleotide» also refers to the modified polynucleotides.

The polynucleotides of the present invention may be isolated or purified from their natural environment. The polynucleotides of the present invention may be also prepared by chemical synthesis or by conventional molecular biology techniques as described by Sambrook, Fristsch and Maniatis, in their book entitled «Molecular cloning: a laboratory manual», edition: Cold Spring Harbor Laboratory Press, Cold Spring Harbor, N.Y., 1989.

The invention also concerns polynucleotides capable of selectively hybridizing with the polynucleotide according to any one of the sequences SEQ ID No. 17 to SEQ ID No. 32

In the context of the present invention, a selective hybridization is performed under medium stringency conditions and preferably under high stringency conditions. Sequence capable of selectively hybridizing means, according to the invention, the sequences which hybridize with the sequence of reference at a level significantly greater than the background noise. The level of the signal generated by the interaction between the sequence capable of selectively hybridizing and the reference sequences is generally 10 times, preferably 100 times more intense than that of the interaction of the other DNA sequences generating the background noise. The stringent hybridization conditions allowing a selective hybridization are known to those skilled in the art. In general, the hybridization and washing temperature is lower of at least 5° C. than the Tm of the reference sequence at a given pH and a given ionic strength. Typically, the hybridization temperature is of at least 30° C. for a polynucleotide from 15 to 50 nucleotides and at least 60° C. for a polynucleotide of more than 50 nucleotides. For example, the hybridization is performed in the following buffer: 6×SSC, 50 mM Tris-HCl (pH 7.5), 1 mM EDTA, 0.02% PVP, 0.02% Ficoll, 0.02% BSA, 500 µg/ml denatured salmon sperm DNA. The washings are for example carried out successively at low stringency in a buffer 2×SSC, 0.1% SDS, at medium stringency in a buffer 0.5×SSC, 01% SDS and at high stringency in a buffer 0.1×SSC, 0.1% SDS. The hybridization can of course be performed according to other usual methods known to those skilled in the art (see in particular Sambrook, Fristsch and Maniatis, in their book entitled «Molecular cloning: a laboratory manual», edition: Cold Spring Harbor Laboratory Press, Cold Spring Harbor, N.Y., 1989). Preferably, the polynucleotides selectively hybridizing to a reference polynucleotide preserve the function of the reference sequence. In this case, the polynucleotides selectively hybridizing with the polynucleotide according to any one of the sequences SEQ ID No. 17 to SEQ ID No. 32. encode for an anti-microbial activity.

The invention generally relates to the polynucleotides encoding for the peptides of the invention. Due to the degeneration of the genetic code, different polynucleotides can encode for the same polypeptide.

The present invention also concerns an expression cassette characterized in that it comprises in the direction of the transcription, a promoter functional in a host organism, a polynucleotide as defined hereinabove and a terminator sequence functional in said host organism.

The present invention further concerns a vector comprising a polynucleotide as defined hereinabove and/or an expression cassette as defined hereinabove.

The present invention also concerns cloning or expression vectors for the transformation of a host organism comprising at least one polynucleotide or an expression cassette according to the present invention. This vector may in particular correspond to a plasmid, a cosmid, a bacteriophage or a virus into which is inserted a polynucleotide or an expression cassette according to the invention. The construction techniques of these vectors and of insertion of a polynucleotide of the invention into these vectors are known to those skilled in the art. Generally, any vector capable of holding, self-replicating or spreading into a host cell in order to induce in particular the expression of a polynucleotide or a peptide can be used. Those skilled in the art will select appropriate vectors depending on the host organism to be transformed, and depending on the implemented transformation technique.

The vectors of the present invention are in particular used to transform a host organism for the purpose of the replication of the vector and/or the expression of a peptide according to the invention in the host organism.

The invention also concerns a method for preparing a peptide according to the invention comprising the following steps:
transforming a host organism with an expression vector comprising an expression cassette according to the invention and/or with a polynucleotide according to the invention,
isolating the peptides produced by the host organism.

The present invention also concerns a host organism transformed with a polynucleotide as defined hereinabove, an expression cassette as defined hereinabove and/or a vector as defined hereinabove.

The present invention also relates to a process for transforming a host organism by integrating into said host organism of at least one polynucleotide, of at least one expression cassette or of at least one vector according to the invention. The polynucleotide may be integrated into the genome of the host organism or replicate in a stable manner in the host organism. The methods for transforming host organisms are known to those skilled in the art and widely described in the literature.

«Host organism» means in particular according to the invention any lower or higher mono- or multicellular organism, in particular selected from the bacteria, the yeasts and the fungi. In particular, «host organism» means a non-human organism. Advantageously, the yeasts are selected from, for example *Pichia pastoris, Saccharomyces cerevisae, Yarrowia lipolytica* and *Schwanniomyces occidentalis*. The fungi are for example selected from the *Aspergillus*, the *Trichoderma* and the *Penicilliums*, preferably from *Penicillium funiculosum, Trichoderma reesei, Aspergillus niger, Aspergillus awamori, Aspergillus kawachii* and *Trichoderma koningii*. In one embodiment of the invention, the host organism is a strain of *Penicillium funiculosum* in which a peptide is expressed or over-expressed according to the invention. In another embodiment, the host organism is a strain of *Debaryomyces castellii* in which a peptide is expressed or over-expressed according to the invention. In yet another embodiment, the host organism is a strain of Enterobacteriaceae or *Corynebacterium* and more particularly *Escherichia coli, Bacillus subtilis, Corynebacterium glutamicum*, in which a peptide is expressed or over-expressed according to the invention.

The techniques of construction of vectors, of transformation of host organisms and of expression of heterologous proteins in these organisms are widely described in the literature in particular Sambrook, Fristsch and Maniatis, in the book entitled «Molecular cloning: a laboratory manual», edition: Cold Spring Harbor Laboratory Press, Cold Spring Harbor, N.Y., 1989 or by Ausubel et al., in the book entitled «Current Protocols in Molecular Biology», edition: Greene Publishing Associates, Inc., and John Wiley and Sons, NY, 1992.

The invention also concerns a preparation process of a peptide having an antimicrobial activity according to the invention, said process comprising the following steps:
culturing a strain of *Arthrobacter gandavensis* or a transformed host organism according to the invention under conditions for inducing the expression of the peptide, and
recovering the culture supernatant (or fermentation must) comprising the peptide.

The separation of the peptide from the culture supernatant can be performed by the load, the size and/or the hydrophobicity. Those skilled in the art know the different techniques allowing the separation depending on the load, the size and/or the hydrophobicity of the different constituents of a medium.

This culture supernatant or fermentation must may then be concentrated or lyophilized for the formulation of a food additive or an animal feed. The process may comprise additional steps of purification of the antimicrobial substance from the culture supernatant.

If the host organism does not secrete the antimicrobial substance in the culture medium, an additional step of breakage of the cells and purification of the cellular extract may be necessary.

The present invention also concerns a composition comprising a peptide as defined hereinabove, a host organism as defined hereinabove, a strain as defined hereinabove, a fermentation must of a host organism as defined hereinabove or a fermentation must of a strain as defined hereinabove. According to one embodiment of the present invention, the composition is in the form of liquid or in the form of powder.

These compositions comprise different ingredients. In the form of liquid, they may comprise for example another antimicrobial agent, for example sorbic acid or a sorbic acid salt, benzoic acid or a benzoic acid salt, fumaric acid or a fumaric acid salt. The compositions of the invention may further comprise sorbitol. Sorbitol is a stabilizing and formulation agent. The compositions of the invention may also comprise antifreeze agents, for example ethylene glycol, glycerol, propylene glycol and propane-1,2-diol.

The compositions of the present invention comprise at least one peptide according to the invention but may also comprise other substances such as vitamins, other active principles, amino acids or mineral salts.

The compositions in the form of powder comprise a support. This support can be selected from wheat flour, starch, maltodextrin, gypsum and corn cobs.

The compositions according to the invention have an antimicrobial activity. They provide alternative solutions to the use of antibiotics. They can for example be used in animal husbandry or as a drug for humans.

The present invention also concerns a nutritional additive comprising a peptide as defined hereinabove, a host organism as defined hereinabove, a strain as defined hereinabove, a fermentation must of a host organism as defined hereinabove or a fermentation must as defined hereinabove.

According to one embodiment of the present invention, the additive is in the form of liquid or in the form of powder.

The present invention also concerns an animal feed characterized in that it comprises a nutritional base for animals and a nutritional additive as defined hereinabove.

These foods are usually in the form of flours or granules into which are incorporated the compositions having an antimicrobial activity.

In the context of the present invention, the term feed means everything which can be used for animal food. Nutritional base means everything which constitutes the main part of the animal food ration, consisting by way of example of a mixture of cereals, proteins and fats of animal and/or plant origin. Usually, these nutritional bases comprise, for example, corn, wheat, and soybeans. These nutritional bases are adapted to the needs of different animal species for which they are intended. It may for example include poultry (laying hens, broil chickens, turkeys and ducks) or pigs (growing and finishing pigs, piglets, sows).

The invention relates to the use of at least one peptide as defined hereinabove, at least one fermentation must of a strain and/or at least one fermentation must of a host organism as defined hereinabove, and/or at least one strain or a host organism as described hereinabove for the preparation of a nutritional additive, a food or a drug.

The peptide according to the invention, the fermentation must of a strain or of a host organism as defined hereinabove, the strain or the host organism as described hereinabove can be used as a drug.

The peptide according to the invention, the fermentation must of a strain or of a host organism as defined hereinabove, the strain or the host organism as described hereinabove can be used to prevent or to treat gastro-intestinal diseases in humans Particularly, the peptide according to the invention, the fermentation must of a strain or of a host organism as defined hereinabove, the strain or the host organism as described hereinabove may be used for the prevention and/or the treatment of intestinal dysbacteriosis, in particular necrotic enteritis in monogastric animals, in particular poultry and pigs The present invention also relates to the use of at least one peptide as defined hereinabove, at least one fermentation must of a strain or of a host organism as defined hereinabove, and/or at least of a strain or of a host organism, of a nutritional additive according to the invention or of a food as described hereinabove to improve the growth performances of animals, in particular chicken.

The present invention also relates to the use of at least one peptide as defined hereinabove, at least one fermentation must of a strain according to the invention and/or a fermentation must of a host organism as defined hereinabove, and/or at least one strain according to the invention and/or a host organism and/or a nutritional additive according to the invention and/or of a food as described hereinabove to improve the zootechnical performances of breeding animals.

In the context of the present invention, the improvement of the zootechnical performances of breeding animals comprises, but is not limited to, the increase of the weight gain of animals, the decrease of the consumption index, the decrease of the mortality and morbidity, the homogeneity of animals, the improvement of carcass yield/meat yield, the improvement of digestibility of the nutrients, the improvement of immune status of animal, the reduction of the negative effects of a pathogen infection (*Clostridium perfingens, Clostridium difficile, E. coli, Salmonella* sp., Campylobacter sp.) or even the improvement of the use of the nutrients and therefore reduction of the excretion of waste.

The present invention will be illustrated by the following examples

EXAMPLE 1: ISOLATION OF THE BACTERIAL STRAINS RUMC+

The search of cultivable strains harboring the rumC-like genes was undertaken from the cecal and ileal microbiota of pigs.

Figure 1:
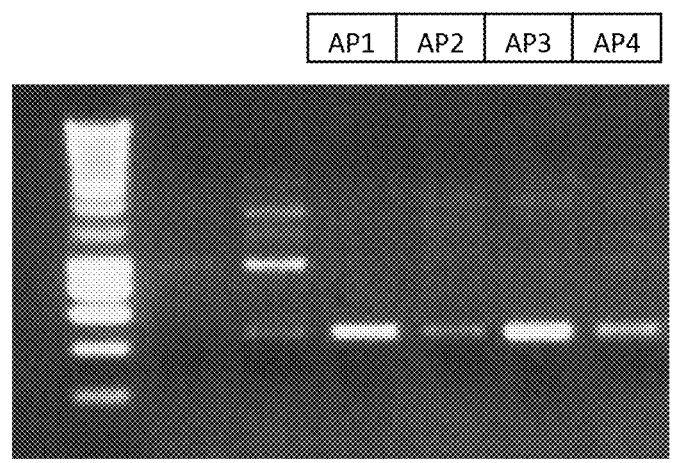
FIG. 1: Detection of the gene rumC1 by PCR

In a first stage, the bacteria are cultured in the following media:
M17: promoting the lactococci
LB: allowing the growth of Bacillus sp. and enterococci
BEA: medium counter-selecting the Bacteroides group The clones are then selected for their ability to inhibit the growth of Clostridium perfringens. The presence of the genes rumC is therefore highlighted by PCR (FIG. 1).

TABLE 1

List of primers used to amplify the different target DNA fragments

| pair of primers | Hybridization Temperature ($T_{opt}$) | Size of the amplified fragment | Target gene(s) |
| --- | --- | --- | --- |
| FC1 (SEQ ID No. 33)-RC1(SEQ ID No. 34) | 55° C. | 700 pb | rumC1 |
| FC2C3 (SEQ ID No. 35)-RC2C3(SEQ ID No. 36) | 60° C. | 800 pb | rumC2-rumC3 |
| FC4C5 (SEQ ID No. 37)-RC4C5(SEQ ID No. 38) | 55° C. | 400 pb | rumC4-rumC5 |

Four strains were retained: AP1, AP2, AP3 and AP4.

EXAMPLE 2: IDENTIFICATION OF THE RETAINED STRAINS 2.1 rDNA 16S

A fragment (about 1550 bp) of the gene encoding for rRNA 16S (corresponding to the positions 8-1541 in the numbering system of Escherichia coli) was amplified by PCR using conserved primers (16F8: 5'-AGAGTTTGATC-CTGGCTGAG-3' (SEQ ID No. 39) and 16R1541: 5'-AAGGAGGTGATCCAGCCGCA-3') (SEQ ID No. 40) and then sequenced.

The sequences obtained were subjected to a comparison in the databanks using a research program of sequence homology of the type «BLAST»

Strain AP1 (SEQ ID No.)=>99.45% of identity with Arthrobacter gandavensis R 5812

Strain AP2 (SEQ ID No.)=>99.37% of identity with Arthrobacter gandavensis R 5812

Strain AP3 (SEQ ID No.)=>99.44% of identity with Arthrobacter gandavensis R 5812

Strain AP4 (SEQ ID No.)=>99.31% identity with Arthrobacter gandavensis R 5812

2.2. PFGE Identification

Figure 2:
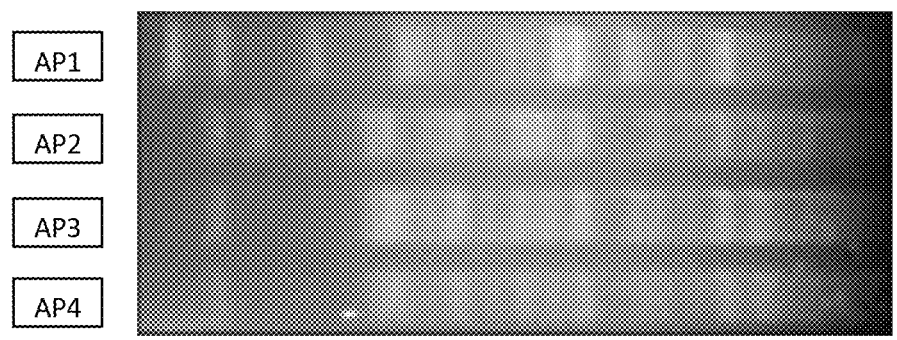
FIG. 2: Chromosomal profile by pulsed-field gel electrophoresis of the strains AP1, AP2, AP3 and AP4.

The strains AP1, AP2, AP3 and AP4 belonging to the genus Arthrobacter must be genetically differentiated at the genetic level. The reference technique for identifying at the intra-specific level of the bacterial strains consists in establishing their chromosomal profile by pulsed-field gel electrophoresis (FIG. 2) (Analysis Report No: LR251012—Biocéane).

The strains AP3 and AP4 appear identical. However, the sequencing of the rumC genes, as well as their reduced peptide sequences seems, for its part, to indicate that AP3 and AP4 are two distinct strains (see Example 4, point 4.2).

EXAMPLE 3: CHARACTERIZATION OF THE STRAINS 3.1 Resistance to pH and to Bile Salts The strains are subjected to two treatments to determine their resistance to the acidity and to the bile salts.

Acidity: buffer NaCl 0.85%, pH2, containing pepsin (1 mg/mL).

Isotonic buffer bile salts ($K_2HPO_4$ 1.24%, $H_2PO_4$ 0.76%, trisodium citrate 0.1%, $[NH_4]_2SO_4$ 0.6%, pH6.7) containing 0.2% of bile salts (50% sodium cholate, 50% sodium deoxycholate)

TABLE 2

Percentage of survival of the different strains

|  | AP1 | AP2 | AP3 | AP4 |
| --- | --- | --- | --- | --- |
| Acidity | 0% | 15% | 12% | 90% |
| BS | 0% | 10% | 8% | ND |

BS: Bile salts;
ND: Not determined

The strain AP4 resists better the conditions imitating the gastric medium. Generally, all the strains are more sensitive to the bile salts but the survival is however sufficient, except for the strain AP1.

3.2 Fermentation Parameters

The analysis of their fermentation parameters was performed on a culture supernatant obtained after growth in BHI-YH in semi-anaerobiosis (In vivo analysis© Labs).

TABLE 3

Assay of the fermentation parameters

|  | AP1 | AP2 | AP3 | AP4 | BHI-YH |
| --- | --- | --- | --- | --- | --- |
| Lactic acid % | 0.01 | 0.01 | 0.01 | 0.02 | 0.04 |
| Ammonia nitrogen g/L | <0.05 | <0.05 | <0.05 | <0.05 | <0.05 |
| Fumaric acid % | <0.01 | <0.01 | <0.01 | <0.01 | <0.01 |
| Acetic acid g/L | 0.16 | 0.14 | 0.13 | 0.15 | 0.15 |
| Propionic acid g/L | <0.1 | <0.1 | <0.1 | <0.1 | <0.1 |

TABLE 3-continued

Assay of the fermentation parameters

|  | AP1 | AP2 | AP3 | AP4 | BHI-YH |
|---|---|---|---|---|---|
| Isobutyric acid g/L | <0.1 | <0.1 | <0.1 | <0.1 | <0.1 |
| Butyric acid g/L | <0.1 | <0.1 | <0.1 | <0.1 | <0.1 |
| Isovaleric acid g/L | <0.1 | <0.1 | <0.1 | <0.1 | <0.1 |
| Valeric acid g/L | <0.1 | <0.1 | <0.1 | <0.1 | <0.1 |

As expected, it is difficult to evaluate the fermentation parameters for the strains *Arthrobacter*. The culture conditions do not allow highlighting the production of any metabolite produced by the fermentation. The presence of propionic acid, isobutyric acid, butyric acid, isovaleric acid and valeric acid has also been checked. However none of the four strains appear to be productive in our culture conditions.

3.3 Tests of Survival to Temperature

The strains are sensitive to the high temperatures. Indeed, none survives beyond 70° C.

According to these results, it is hardly possible to provide for an addition of these strains during the granulation.

3.4 Tests of Survival in Water and Food

The strain *Arthrobacter* sp. AP4 survives very well in water (Table 4 hereinafter). It even seems that it is able to grow in these conditions. Indeed, after seven days in water, the bacterial population has doubled.

TABLE 4

Percentage of survival in water

|  | D1 | D2 | D3 | D4 | D7 |
|---|---|---|---|---|---|
| AP4 | 134% | 144% | 130% | 166% | 206% |

Figure 3:
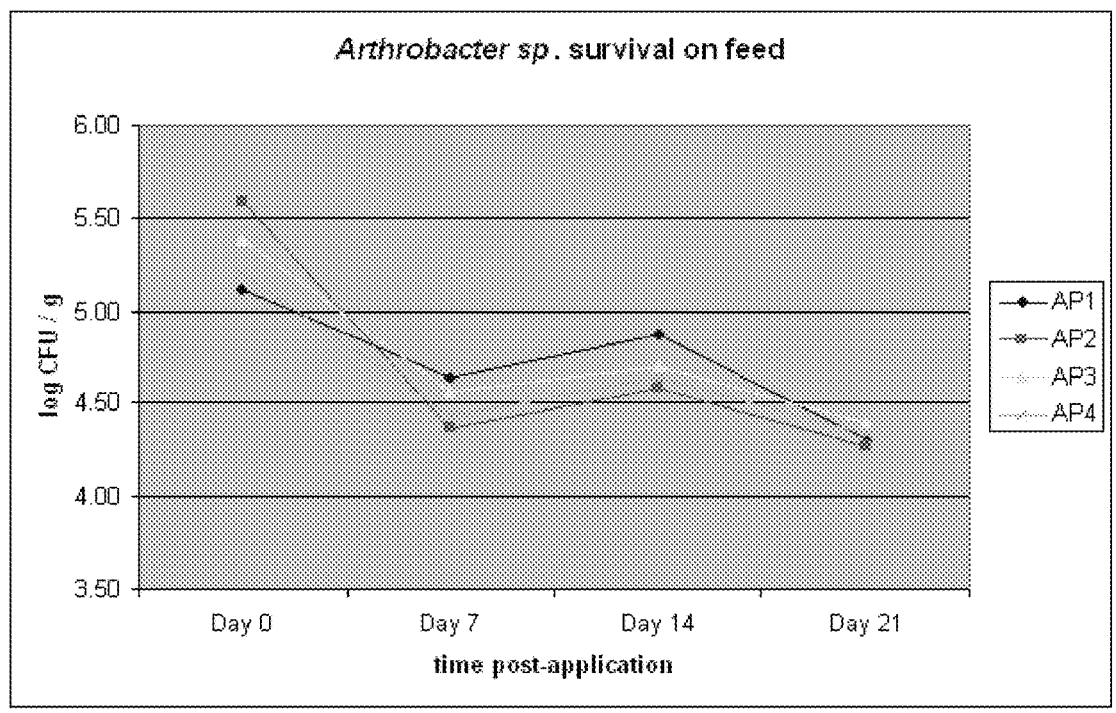
FIG. 3: Percentage of survival in the food of the strains AP1, AP2, AP3 and AP4
Figure 4:
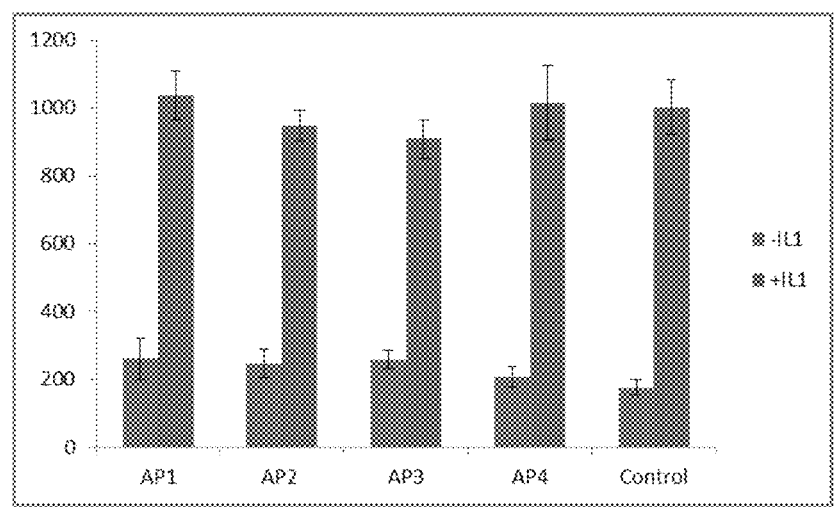
FIG. 4: Assay of interleukins IL8 by ELISA in the culture supernatant of the cells Caco-2 after contact with the bacteria in the presence or absence of IL1

In food, the population remains relatively stable even after 21 days (FIG. 3). According to these results, the addition of the strains in the drinking water as well as in food is possible.

3.5 Anti-Inflammatory Potential

The modulation of the inflammatory profile is estimated by assay of interleukins IL8 by ELISA in the culture supernatant of the Caco-2 cells (intestinal cell line) after contact with the bacteria in the presence or absence of IL1 (induction molecule of the inflammation).

These results were obtained on the supernatants of cells cultured in well. The bacteria present no pro-inflammatory activity (low secretion of IL8 in the absence of IL1) nor anti-inflammatory activity (amount of IL8 in the presence of IL1 identical to the control).

The experiment was repeated with the strain AP4 but with Caco-2 cells cultured on filter. In this case, this strain has a pro-inflammatory activity.

3.6 Enzymatic Profiles

The API ZYM system is a semi-quantitative method of research of enzymatic activities. The enzymatic tests are inoculated with a dense bacterial suspension.

TABLE 5

Results of the readings of the strips Api Zym

|  | AP1 | | AP2 | | AP3 | | AP4 | |
|---|---|---|---|---|---|---|---|---|
|  | I | II | I | II | I | II | I | II |
| 1. Control without a substrate | — | — | — | — | — | — | — | — |
| 2. Alkaline phosphatase | — | — | — | — | — | — | — | — |
| 3. Esterase (C4) | 5 | 5 | 5 | 4 | 5 | 4 | 5 | 5 |
| 4. Esterase lipase (C8) | 1 | 3 | 4 | 4 | 3 | 4 | 3 | 5 |
| 5. Lipase (C14) | — | — | — | — | — | — | — | — |
| 6. Leucine arylamidase | 5 | 5 | 5 | 5 | 5 | 5 | 5 | 5 |
| 7. Valine arylamidase | 3 | 1 | 4 | 1 | 4 | 1 | 4 | 1 |
| 8. Cystine arylamidase | 3 | — | 4 | — | 4 | — | 4 | — |
| 9. Trypsin | — | — | — | — | — | — | — | — |
| 10. Alpha-Chymotrypsine | — | — | — | — | — | — | — | — |
| 11. Acid Phosphatase | 3 | 3 | 4 | 3 | 4 | 2 | 4 | 3 |
| 12. Naphtol phosphohydrolase | — | 1 | — | 1 | — | 1 | — | 1 |
| 13. Alpha-galactosidase (melibiase) | — | — | — | — | — | — | — | — |
| 14. Beta-galactosidase (lactase) | — | — | — | — | — | — | — | — |
| 15. Beta-glucuronidase (hyaluronidase) | — | — | — | — | — | — | — | — |
| 16. Alpha-glucosidase (maltase) | 2 | 1 | — | — | — | — | — | — |
| 17. Beta-glucosidase (cellulase) | — | — | — | — | — | — | — | — |
| 18. N-acetyl-beta-glucosaminidase (chitinase) | — | — | — | — | — | — | — | — |
| 19. Alpha-mannosidase | — | — | — | — | — | — | — | — |
| 20. Alpha-fucosidase | — | 1 | — | — | — | — | — | — |

I: first assay;
II: second assay

Some activities are indisputably found regardless of the used strain. This is the case of the esterase, esterase lipase, leucine arylamidase, valine arylamidase and acid phosphatase. Some activities do not seem very stable, such as for the cystine arylamidase.

The strain AP1 presents a profile different from the other *Arthrobacter* in the use of the maltose and fucose for example.

3.7 Resistance to Antibiotics

A first assay was conducted in the laboratory. The antimicrobial susceptibility testing was performed using antibiotic diffusion discs (BBL™ Sensi-Disc™ Susceptibility Test Discs).

The tested antibiotics were used in the following quantities: Bacitracin 10 µg, erythromycin 15 µg, penicillin G 10 µg, ampicillin 10 µg, vancomycin 30 µg, streptomycin 300 µg, chloramphenicol 30 µg, ciprofloxacin 5 µg, fosfomycin 200 µg, rifamycin 25 µg, and trimethoprim/sulfamethoxazole 1.25 µg/23.75 µg. The results of the antimicrobial susceptibility testing are subjected to a reading abacus in order to determine the level of sensitivity of the strain relative to the measured inhibition diameter.

The 4 strains of *Arthrobacter* are sensitive to all the tested antibiotics.

TABLE 6 sensitivity to antibiotics

|  | AP1 | AP2 | AP3 | AP4 |
|---|---|---|---|---|
| Ampicillin | S | S | S | S |
| Erythromycin | S | S | S | S |
| Gentamicin | S | S | S | S |
| Kanamycin | S | S | S | S |
| Streptomycin | R | R | R | R |
| Tetracyclin | R | S | S | S |
| Chloramphenicol | R/S | R/S | S | S |
| Vancomycin | S | S | S | S |
| Ciprofloxacin | ND* | ND* | ND* | ND* |

TABLE 6-continued sensitivity to antibiotics

| | AP1 | AP2 | AP3 | AP4 |
|---|---|---|---|---|
| Linezolid | ND* | ND* | ND* | ND* |
| Clindamycin | R | S | S | S |
| Tylosin | ND* | ND* | ND* | ND* |

*ND: not determined because of the absence of break-point

According to these tests, all the strains are resistant to the Streptomycin. The strain AP1 is the one which is the most resistant.

3.8 Adhesion Tests

The bacterial adhesion is estimated on the Caco-2 cells (epithelial cell line).

TABLE 7

Bacterial count and adhesion rates

| Strains | $CFU_I$ | $CFU_A$ |
|---|---|---|
| AP1 | $4.90 \cdot 10^8$ | $1.50 \cdot 10^3$ |
| AP2 | $1.50 \cdot 10^9$ | $3.00 \cdot 10^3$ |
| AP3 | $1.75 \cdot 10^8$ | $6.00 \cdot 10^3$ |
| AP4 | $1.42 \cdot 10^9$ | $3.00 \cdot 10^4$ |

$CFU_I$: initial enumeration
$CFU_A$: enumeration after adhesion

Although low, all our strains have adhesiveness to the intestinal cells. The strains AP3 and AP4 seem to adhere more effectively.

EXAMPLE 4 VALIDATION OF THE CONCEPT 4.1 Harmlessness of the Strains

In a first step, the bacteria were observed by electron microscopy in order to check the absence of morphological character associated with the pathogenicity.

The morphology of the cells is variable (coccoid sticks), which is consistent with the characterization of the genus *Arthrobacter*. The cells are devoid of flagella and pili.

In a second step, an in vivo test was established. $10^7$ bacteria were intragastrically administered to germfree mice (3 animals per strain). Daily and for 5 days, a sampling of faeces is performed. An analysis of these saddles by optical microscopy allowed to confirm the presence of the bacteria during at least 4 days, highlighting their survival in the digestive tract. An absence of mortality, intestinal lesions and clinical signs (prostration, diarrhea . . . ) should be noted. These results support the experimentation on the cell line Caco-2 (Absence of lysis or cell detachment).

4.2 Sequencing of the Genes rumC

The sequences of the different rumC-like genes present in our strains were compared to the sequences of the strain *R. gnavus* E1 (See Appendices).

TABLE 8

Percentage of identity of the rumC-like genes relative to the *R. gnavus* E1 genes (the identifiers of sequences in the table hereinafter correspond to the sequences identified in the strains AP1 to AP4).

| | AP1 | AP2 | AP3 | AP4 |
|---|---|---|---|---|
| rumC1 | 78.12 (SEQ ID No 17) | 99.48 (SEQ ID No 22) | 93.23 (SEQ ID No 27) | 98.44 (SEQ ID No 30) |

TABLE 8-continued

Percentage of identity of the rumC-like genes relative to the *R. gnavus* E1 genes (the identifiers of sequences in the table hereinafter correspond to the sequences identified in the strains AP1 to AP4).

| | AP1 | AP2 | AP3 | AP4 |
|---|---|---|---|---|
| rumC2 | 97.92 (SEQ ID No 18) | 55.73 (SEQ ID No 23) | 86.46 (SEQ ID No 28) | 84.9 (SEQ ID No 31) |
| rumC3 | 100 (SEQ ID No 19) | 44.79 (SEQ ID No 24) | 89.06 (SEQ ID No 29) | 89.06 (SEQ ID No 32) |
| rumC4 | 60.98 (SEQ ID No 20) | 75.14 (SEQ ID No 25) | / | / |
| rumC5 | 52.2 (SEQ ID No 21) | 66.88 (SEQ ID No 26) | / | / |

The conservation of the genes is different depending on the strains. The rumC1 gene is the one that is the more conserved. Generally, the rumC4 and rumC5 genes are very divergent, even too divergent, to be sequenced for the strains AP3 and AP4.

The same analysis has been performed by comparing the deduced peptide sequences (See appendices).

TABLE 9

Percentage of identity of the peptide sequences deduced relative to *R. gnavus* E1 (the identifiers of sequences shown in the table hereinafter correspond to the sequences identified in the strains AP1 to AP4).

| | AP1 | AP2 | AP3 | AP4 |
|---|---|---|---|---|
| RumC1 | 55.56 (SEQ ID No 1) | 98.41 (SEQ ID No 6) | 62.3 (SEQ ID No 11) | 75.81 (SEQ ID No 14) |
| RumC2 | 79.37 (SEQ ID No 2) | 25.4 (SEQ ID No 7) | 77.78 (SEQ ID No 12) | 76.19 (SEQ ID No 15) |
| RumC3 | 100 (SEQ ID No 3) | 3.17 (SEQ ID No 8) | 92.06 (SEQ ID No 13) | 92.06 (SEQ ID No 16) |
| RumC4 | 7.69 (SEQ ID No 4) | 14.29 (SEQ ID No 9) | | |
| Rumc5 | 15.38 (SEQ ID No 5) | 33.96 (SEQ ID No 10) | | |

Generally the same conclusions can be drawn. The identities of the deduced sequences are lower than the identities of the genes. In some cases, the peptide sequences are too distant (or truncated; see appendices) to affirm an activity (RumC2_AP3 and RumC4_AP1 for example).

4.3 Activity Test

The activity tests are carried out with the bacterial culture supernatants against the strain *Clostridium perfringens*.

Figure 5:
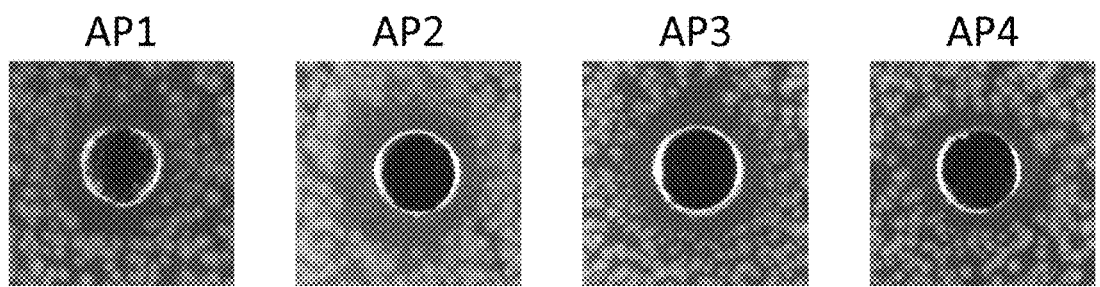
FIG. 5: The activity tests with the bacterial culture supernatants against the strain Clostridium perfringens
Figure 6:
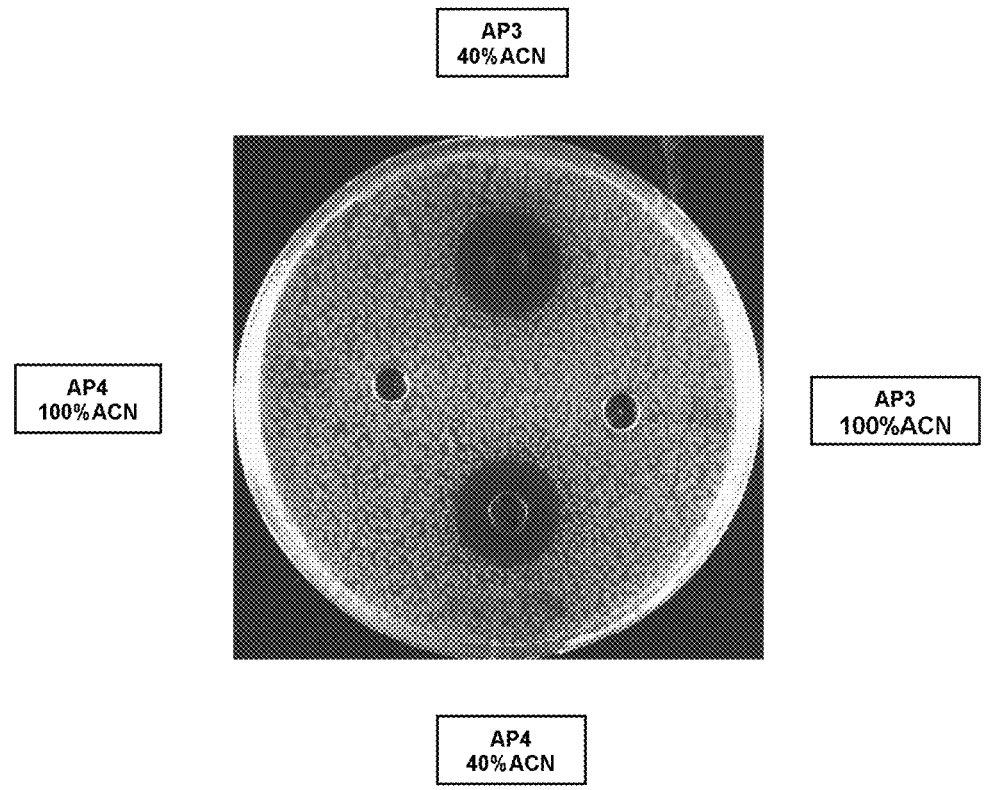
FIG. 6: an activity anti-C. perfringens after a first pre-purification step has been carried out: purification of supernatants on Sep-Pak column with an elution at 40% of acetonitrile (ACN, see WO2008/152252).
Figure 7:
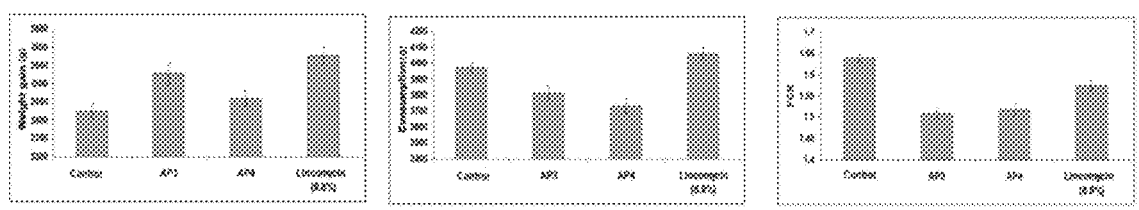
FIG. 7: An illustration of the data set forth in Table 10.

The four strains have an anti-*C. perfringens* activity (FIG. 5). In order to limit the action of an organic acid, the supernatants are neutralized prior to the test. Two tests were carried out in order to confirm the idea that the inhibition of *C. perfringens* is due to a «RumC-like» activity. In a first step, supernatants were heated for 10 min at 95° C. before the test. The activity is conserved as is the case for RumC. In a second step, the first pre-purification step was carried out (see WO 2008/152252): purification of the supernatants on column Sep-Pak with an elution with 40% of acetonitrile (ACN, FIG. 6). In this case, the activity is also identified.

4.4 Evaluation of the Probiotic Properties of the Strains of *Arthrobacter* in Vivo The evaluation of the effect of the strains AP3 and AP4 on the growth performances of the broil chickens (weight gain, consumption and consumption index) was carried out under conditions called challenging diet. This diet is a corn-based diet with a standard protein content (23%) for 14 days followed by a high protein (26% of protein), wheat- and barley-based diet, therefore rich in fibers, from 14 to 35 days. This challenging diet corresponds to the control diet of table 10).

The strains AP3 and AP4 were sprayed onto the feed at a concentration allowing the ingestion of $10^8$ CFU per day and per animal, from the first day, and this, throughout the duration of the assay, namely 35 days. These diets correspond respectively to the mentions «AP3» and «AP4» in the table 10.

The diet «Lincomycin (8.8%)» corresponds to a challenging diet which is added to the lycomycin up to 8.8% (i.e. 5.25 g per ton of feed).

These four treatments were performed on batches of 15 chickens were repeated 12 times (namely 720 chickens in total).

TABLE 10 in vivo Results.

|  | Weight gain (g) | ET | % | Consumption (g) | ET | % | IC | ET | % | Mortality |
|---|---|---|---|---|---|---|---|---|---|---|
| Control | 2425 | 21.4 |  | 3974 | 28.0 |  | 1.639 | 0.009 |  | 3.3% |
| AP3 | 2527 | 28.2 | 4.2% | 3815 | 42.6 | −0.4% | 1.51 | 0.012 | −7.9% | 3.3% |
| AP4 | 2460 | 21.5 | 1.4% | 3733 | 43.3 | −6.1% | 1.518 | 0.015 | −7.4% | 1.1% |
| Lincomycin (8.8%) | 2577 | 22.4 | 6.3% | 4057 | 37.7 | 2.1% | 1.575 | 0.013 | −3.9% | 1.7% |

ET: Standard Deviation;
IC: Consumption Index (consumption of feed required for the increase of the weight gain by 1 kg, IC = Consumption/Weight Gain);
%: Percentage of improvement compared to the control;
Consumption: feed consumption by the animals over the entire assay The two tested strains, AP3 and AP4, have similar and positive effects on the growth performances of broil chickens. They allow a decrease of the consumption index by 7 to 8% due to both an increase in the weight gain and a decrease in the consumption.

---

The invention claimed is:

1. A method of providing antibacterial activity against *Clostridium perfringens*, comprising administering a composition including a bacterial strain of *Arthrobacter gandavensis* strain selected from the group consisting of strain AP1 (DSMZ DSM 28444), strain AP2 (DSMZ DSM 28445), strain AP3 (DSMZ DSM 28446), and strain AP4 (DSMZ DSM 28447) to a non-human animal or human, wherein the bacterial strain produces at least one peptide selected from the group consisting of SEQ ID NOS: 1-16.

2. The method of claim 1, wherein the composition is a liquid or powder.

3. The method of claim 1, wherein the composition is a nutritional additive and is administered to a non-human animal.

4. The method of claim 1, wherein the composition is an animal feed that comprises a nutritional base and a nutritional additive comprising the peptide or bacterial strain, and the animal feed is administered to a non-human animal.

5. The method of claim 1, wherein the composition is a food or drug, and is administered to a human.

6. The method of claim 1, wherein the composition is administered to a non-human animal to treat or reduce the likelihood of developing intestinal dysbacteriosis.

7. The method of claim 1, wherein the composition is administered to a monogastric animal to treat or reduce the likelihood of developing necrotic enteritis.

8. The method of claim 1, wherein the composition is administered to a breeding animal to improve growth performance.

9. The method of claim 1, wherein the composition is administered to a breeding animal to improve zootechnical performance.

* * * * *

SEQUENCE LISTING

```
<160> NUMBER OF SEQ ID NOS: 40

<210> SEQ ID NO 1
<211> LENGTH: 63
<212> TYPE: PRT
<213> ORGANISM: Arthorbacter gandavensis

<400> SEQUENCE: 1

Met Asn Ile Ile Ala Thr Tyr Gln Ser Leu Lys Glu Asn Gln Asn Gln
1               5                   10                  15

Asp Tyr Thr Pro Arg Leu Phe Val Phe Ala Gly Lys Ala Val Ala Asn
            20                  25                  30

Ser His Asn Ala Gly Pro Ala Tyr Cys Val Gly Tyr Cys Gly Asn Asn
        35                  40                  45

Gly Val Val Thr Arg Asn Ala Asn Ala Asn Val Ala Lys Thr Ala
    50                  55                  60

<210> SEQ ID NO 2
<211> LENGTH: 64
<212> TYPE: PRT
<213> ORGANISM: Arthorbacter gandavensis

<400> SEQUENCE: 2

Met Arg Lys Ile Val Ala Gly Lys Leu Gln Thr Gly Ala Asp Phe Glu
1               5                   10                  15

Gly Ser Lys Gly Gly Cys Lys Cys Ser Gly Gly Ala Val Val Glu Asn
            20                  25                  30

Ser His Asn Ala Gly Pro Ala Tyr Cys Val Gly Tyr Cys Gly Asn Asn
```

```
            35                  40                  45

Gly Gly Asp Asn Lys Lys Cys Glu Cys Tyr Ser Cys Lys Asn Lys Ile
     50                  55                  60

<210> SEQ ID NO 3
<211> LENGTH: 63
<212> TYPE: PRT
<213> ORGANISM: Arthorbacter gandavensis

<400> SEQUENCE: 3

Met Lys Leu Val Glu Thr Lys Thr Thr Lys Thr Gly Thr Asn Phe Glu
1               5                   10                  15

Gly Asn Arg Ala Gly Cys Ile Cys Asn Gly Thr Val Ala Val Ala Asn
            20                  25                  30

Ser His Asn Ala Gly Pro Ala Tyr Cys Val Gly Tyr Cys Gly Asn Ser
        35                  40                  45

Gly Val Val Thr Arg Asn Ala Asn Ala Asn Val Ala Lys Thr Ala
     50                  55                  60

<210> SEQ ID NO 4
<211> LENGTH: 52
<212> TYPE: PRT
<213> ORGANISM: Arthorbacter gandavensis

<400> SEQUENCE: 4

Trp Lys Leu Asn Met Ser Asp Thr His His Phe Glu Glu Gly Lys Pro
1               5                   10                  15

Gly Arg Gly Gly Arg Val Thr Asn Arg Gly Glu Thr Ile Ile Met Val
            20                  25                  30

Phe Arg Cys Trp Val Glu Cys Gly Pro Ser Asn Tyr Gln Lys Ser Ile
        35                  40                  45

Asn Asn Tyr Glu
     50

<210> SEQ ID NO 5
<211> LENGTH: 52
<212> TYPE: PRT
<213> ORGANISM: Arthorbacter gandavensis

<400> SEQUENCE: 5

Lys Asn Cys Glu Arg Thr Leu Ile Ser Lys Glu Arg Leu Asp Val Leu
1               5                   10                  15

Leu Ser Leu Phe Leu Arg Gly Val Cys Arg Asn Pro Asn Ser Asn Lys
            20                  25                  30

Pro Gly Val Leu Val Val Trp Phe Trp Gly Glu Phe Gly Glu Pro Thr
        35                  40                  45

Arg Asn Asp Met
     50

<210> SEQ ID NO 6
<211> LENGTH: 64
<212> TYPE: PRT
<213> ORGANISM: Arthorbacter gandavensis

<400> SEQUENCE: 6

Met Arg Lys Ile Val Ala Gly Lys Leu Gln Thr Gly Ala Asp Phe Glu
1               5                   10                  15

Gly Ser Lys Trp Gly Cys Val Cys Ser Gly Ser Thr Ala Val Ala Asn
            20                  25                  30
```

```
Ser His Asn Ala Gly Pro Ala Tyr Cys Val Gly Tyr Cys Thr Arg Asn
        35                  40                  45

Asn Gly Val Val Thr Arg Asn Ala Asn Ala Asn Val Ala Lys Thr Ala
    50                  55                  60
```

<210> SEQ ID NO 7
<211> LENGTH: 65
<212> TYPE: PRT
<213> ORGANISM: Arthorbacter gandavensis

<400> SEQUENCE: 7

```
Met Arg Ser Ile Glu Glu Cys Met Glu Thr Trp Ile Leu Glu Cys Arg
1               5                   10                  15

Gly Ser Gly Leu His Val Arg Asn Ala Lys Tyr Gly Arg Thr Pro Val
            20                  25                  30

Ala Lys Ala Ala Val Gly Leu Tyr Arg Glu Ala Arg Lys Ser Gly Gln
        35                  40                  45

Thr Gly Leu Asp Thr Val Gly Asn Ala Asn Ala Asn Leu Ala Arg Thr
    50                  55                  60

Lys
65
```

<210> SEQ ID NO 8
<211> LENGTH: 63
<212> TYPE: PRT
<213> ORGANISM: Arthorbacter gandavensis

<400> SEQUENCE: 8

```
Met Lys Leu Val Gly Gly Phe Pro Pro Gln Ala Ala Ser Ile Lys
1               5                   10                  15

His Leu Gln Gly Ser Met Ala Ala Arg Thr Gln Arg Lys Arg Gly Leu
            20                  25                  30

Leu Cys Gly Glu His Trp Ile Arg Pro Arg Arg Ser Phe Gln Leu Gln
        35                  40                  45

Phe Gly Val Met Met Gln Ala Val Gln Lys Ser His Asn Gln Pro
    50                  55                  60
```

<210> SEQ ID NO 9
<211> LENGTH: 56
<212> TYPE: PRT
<213> ORGANISM: Arthorbacter gandavensis

<400> SEQUENCE: 9

```
Val Arg Glu Ala Leu His Ile Ala Ser Thr Phe Arg Arg Thr Gln Ala
1               5                   10                  15

Val Phe Ala Ala Asp Cys Arg Leu Glu Ile Leu Ile Met Gln Asp Gln
            20                  25                  30

His Ile Val Leu Gly Met Val Glu Arg Trp Ala Val Thr Arg Asn Gln
        35                  40                  45

Asn Tyr Thr Leu Glu Gln Arg Ser
    50                  55
```

<210> SEQ ID NO 10
<211> LENGTH: 53
<212> TYPE: PRT
<213> ORGANISM: Arthorbacter gandavensis

<400> SEQUENCE: 10

```
Leu Gly Thr Ala Lys Pro Ile Lys Thr Gln Asn Asn Phe Glu Gly Asn
1               5                   10                  15
```

-continued

```
Gly Ala Gly Cys Phe Cys Gly Gly Ser Val Ala Ile Gln Ile Leu Ile
            20                  25                  30

Ser Arg Glu Phe Leu Leu Cys Gly Phe Gly Gly Asn Leu Gly Asn Gln
        35                  40                  45

Pro Ala Met Ile Cys
    50

<210> SEQ ID NO 11
<211> LENGTH: 61
<212> TYPE: PRT
<213> ORGANISM: Arthorbacter gandavensis

<400> SEQUENCE: 11

Met Arg Lys Ile Val Ala Gly Lys Leu Gln Thr Gly Ala Asp Phe Glu
1               5                   10                  15

Gly Ser Lys Trp Trp Met Met Gln Trp Arg Cys Ser Ser Arg Asn Ser
            20                  25                  30

His Asn Ala Gly Pro Ala Tyr Cys Val Gly Tyr Cys Gly Asn Asn Gly
        35                  40                  45

Gly Leu Glu Met Leu Met Gln Met Ser Gln Lys Arg His
    50                  55                  60

<210> SEQ ID NO 12
<211> LENGTH: 63
<212> TYPE: PRT
<213> ORGANISM: Arthorbacter gandavensis

<400> SEQUENCE: 12

Met Arg Lys Ile Val Ala Gly Lys Leu Gln Thr Gly Ala Asp Phe Glu
1               5                   10                  15

Gly Ser Arg Ser Gly Cys Val Cys Ser Gly Ser Ala Ala Val Ala Ser
            20                  25                  30

Ser His Tyr Ala Gly Pro Ala Tyr Cys Val Gly Tyr Cys Gly Asn His
        35                  40                  45

Gly Ala Val Thr Arg Asn Ala Asn Tyr Asn Leu Ala Lys Lys Asn
    50                  55                  60

<210> SEQ ID NO 13
<211> LENGTH: 63
<212> TYPE: PRT
<213> ORGANISM: Arthorbacter gandavensis

<400> SEQUENCE: 13

Met Lys Leu Val Glu Thr Lys Thr Thr Lys Thr Gly Thr Asp Phe Glu
1               5                   10                  15

Gly Asn Arg Ala Gly Cys Ile Cys Asn Gly Thr Val Val Ala Asn
            20                  25                  30

Ser His Tyr Ala Gly Pro Ala Tyr Cys Val Gly Tyr Cys Gly Asn Ser
        35                  40                  45

Gly Val Val Thr Arg Asn Ala Asn Ala Asp Leu Ala Arg Thr Ala
    50                  55                  60

<210> SEQ ID NO 14
<211> LENGTH: 62
<212> TYPE: PRT
<213> ORGANISM: Arthorbacter gandavensis

<400> SEQUENCE: 14

Met Ser Asn Ile Leu Ala Gly Lys Leu Gln Thr Gly Ala Asp Phe Glu
```

```
                1               5                      10                      15
            Gly Ser Lys Trp Gly Cys Val Cys Ser Gly Ser Thr Ala Val Ala Asn
                            20                      25                      30

Ser His Asn Ala Gly Pro Ala Tyr Cys Val Gly Tyr Cys Gly Asn Asn
                        35                      40                      45

Gly Val Ser Asp Lys Cys Cys Lys Cys Arg Lys Asn Gly Asn
                        50                      55                      60

<210> SEQ ID NO 15
<211> LENGTH: 63
<212> TYPE: PRT
<213> ORGANISM: Arthorbacter gandavensis

<400> SEQUENCE: 15

Met Arg Lys Ile Val Ala Gly Lys Leu Gln Thr Gly Ala Asp Phe Glu
            1               5                      10                      15

Gly Ser Arg Ser Gly Cys Val Cys Ser Ala Ser Ala Val Ala Ser
                            20                      25                      30

Ser His Tyr Ala Gly Pro Ala Tyr Cys Val Gly Tyr Cys Gly Asn Arg
                        35                      40                      45

Gly Ala Val Thr Arg Asn Ala Asn Tyr Asn Leu Ala Lys Lys Asn
                        50                      55                      60

<210> SEQ ID NO 16
<211> LENGTH: 63
<212> TYPE: PRT
<213> ORGANISM: Arthorbacter gandavensis

<400> SEQUENCE: 16

Met Lys Leu Val Glu Thr Lys Thr Thr Lys Thr Gly Thr Asp Phe Glu
            1               5                      10                      15

Gly Asn Arg Ala Gly Cys Ile Cys Asn Gly Thr Val Ala Val Ala Asn
                            20                      25                      30

Ser His Tyr Ala Gly Pro Ala Tyr Cys Val Gly Tyr Cys Gly Asn Ser
                        35                      40                      45

Gly Val Val Thr Arg Asn Ala Asn Ala Asp Leu Ala Arg Thr Ala
                        50                      55                      60

<210> SEQ ID NO 17
<211> LENGTH: 192
<212> TYPE: DNA
<213> ORGANISM: Arthorbacter gandavensis

<400> SEQUENCE: 17
ttgaacatta ttgccactta tcaatcattg aaagagaacc agaaccaaga ctacacacca      60
cgcttgttcg tctttgccgg taaagcagta gcaaactctc ataatgcagg accggcgtat     120
tgcgtaggat actgtggaaa caacggagta gtgactagaa atgctaatgc aaatgtcgca     180
aaaacggcat aa                                                         192

<210> SEQ ID NO 18
<211> LENGTH: 193
<212> TYPE: DNA
<213> ORGANISM: Arthorbacter gandavensis

<400> SEQUENCE: 18
atgagaaaaa tcgtagcagg aaagttacag acaggagcag actttgaagg cagcaaaggt      60
ggatgtaaat gcagtggcgg tgcagtagta gaaaactctc ataatgcagg accagcgtat     120
```

```
tgcgtgggat actgtggaaa caacggagga gataacaaga aatgcgaatg ctattcttgc      180
aagaacaaaa taa                                                        193

<210> SEQ ID NO 19
<211> LENGTH: 192
<212> TYPE: DNA
<213> ORGANISM: Arthorbacter gandavensis

<400> SEQUENCE: 19
atgaaattag tagaaacaaa acaacaaaaa acaggaacaa actttgaagg gaatagagct      60 ggatgtatttt gtaatggcac tgtagcagta gcaaattctc ataatgcagg accagcatat    120
tgtgttgggt attgcggaaa tagtggagta gtaacaagaa atgcgaatgc aaatgtcgca    180
aaaacagcat aa                                                        192

<210> SEQ ID NO 20
<211> LENGTH: 164
<212> TYPE: DNA
<213> ORGANISM: Arthorbacter gandavensis

<400> SEQUENCE: 20
tggaagctaa attagatgag cgacacacat cactttgaag aaggtaagcc aggccggggt      60
ggccgcgtaa caaacagagg cgaaactatt ataatggtgt ttagatgttg ggtggagtgt    120
gggccctctt agaactatca aaatcaatt ataactatg aaag                       164

<210> SEQ ID NO 21
<211> LENGTH: 159
<212> TYPE: DNA
<213> ORGANISM: Arthorbacter gandavensis

<400> SEQUENCE: 21
caaaaattgt gagagaacac ttatttcaaa ggagagactg gatgtactgc tgtcgctgtt      60
tttgcggggg gtctgtcgca atccaaattc taataagccg ggagttcttg ttgtgtggtt    120
ttggggggaa tttggggaac caacccgcaa tgatatgtt                           159

<210> SEQ ID NO 22
<211> LENGTH: 198
<212> TYPE: DNA
<213> ORGANISM: Arthorbacter gandavensis

<400> SEQUENCE: 22
atgagaaaaa tcgtagcagg aaagttacag acaggagcag actttgaagg cagcaaatgg      60
ggatgtgttt gtagtggaag cacagcagta gcaaactctc ataatgcagg accggcgtat    120
tgcgtaggat actgtacata gagaaacaac ggagtagtga ctagaaatgc taatgcaaat    180
gtcgcaaaaa cggcataa                                                  198

<210> SEQ ID NO 23
<211> LENGTH: 216
<212> TYPE: DNA
<213> ORGANISM: Arthorbacter gandavensis

<400> SEQUENCE: 23
atgaggtcaa tcgaagaatg catggaaact tggatacttg agtgctgaag aggcagtgga      60
ctccatgtgt agcggtgaaa tgcgtagaaa tatggaagaa ccccagtggc gaaggcggca    120
gtcggtctgt actgacgtga ggctcgaaag tctgggtagc aaacaggatt agataccgta    180
ggaaatgcga atgcgaatct tgcaagaaca aaataa                              216
```

<210> SEQ ID NO 24
<211> LENGTH: 210
<212> TYPE: DNA
<213> ORGANISM: Arthorbacter gandavensis

<400> SEQUENCE: 24

| | |
|---|---:|
| atgaaattag ttggagggtt tccgcctcaa gcggccgcta gcattaagca tcttcagggg | 60 |
| agtatggccg caaggtgaac tcaaaggaag cggggcttc tctgcggaga gcattggtaa | 120 |
| atttgaagac cgcgaaggtc cttccagctg cagtttgggg tgatgtaaat gcaggcggtg | 180 |
| cagtagtaga aatctcataa tcagccataa | 210 |

<210> SEQ ID NO 25
<211> LENGTH: 173
<212> TYPE: DNA
<213> ORGANISM: Arthorbacter gandavensis

<400> SEQUENCE: 25

| | |
|---|---:|
| gggtacgcga agcactgcac atcgcttcaa cttttaggag gacgcaggct gtgtttgcag | 60 |
| cggactgtcg acttgaaatt ctcataatgc aggaccagca tattgtgttg ggatggtgg | 120 |
| aaagatgggc agtaaccaga atcaaaatt atactcttga acaaaggtct taa | 173 |

<210> SEQ ID NO 26
<211> LENGTH: 160
<212> TYPE: DNA
<213> ORGANISM: Arthorbacter gandavensis

<400> SEQUENCE: 26

| | |
|---|---:|
| ttaggaacag caaaaccaat aaaaacgcaa ataatttg aaggaaacgg ggctggttgt | 60 |
| ttttgcgggg ggtctgtcgc aatccaaatt ctaataagcc gggagttctt gttgtgtggt | 120 |
| tttgggggga atttggggaa ccaacccgca atgatatgtt | 160 |

<210> SEQ ID NO 27
<211> LENGTH: 194
<212> TYPE: DNA
<213> ORGANISM: Arthorbacter gandavensis

<400> SEQUENCE: 27

| | |
|---|---:|
| atgagaaaaa tcgtagcagg aaagttacag acaggagcag actttgaagg cagcaaatgg | 60 |
| tggatgtaaa tgcagtggcg gtgcagtagt agaaactctc ataatgcagg tccagcgtat | 120 |
| tgcgtgggat actgtggaaa caacggaggg tagtgactag aaatgctaat gcaaatgtcg | 180 |
| caaaaacggc ataa | 194 |

<210> SEQ ID NO 28
<211> LENGTH: 192
<212> TYPE: DNA
<213> ORGANISM: Arthorbacter gandavensis

<400> SEQUENCE: 28

| | |
|---|---:|
| atgagaaaaa tcgtagcagg aaagttacag acaggagcag actttgaagg cagcagaagt | 60 |
| ggatgtgttt gtagtggaag cgcagcagta gcaagctctc attatgcagg accagcatat | 120 |
| tgcgtaggat actgtggaaa ccatggagca gtaacaagaa atgcgaatta taatcttgca | 180 |
| aaaaaaact ag | 192 |

<210> SEQ ID NO 29

```
<211> LENGTH: 192
<212> TYPE: DNA
<213> ORGANISM: Arthorbacter gandavensis

<400> SEQUENCE: 29
atgaaattag tagaaacaaa aacaacaaaa acaggaacag actttgaagg aaatagggct    60
ggatgtattt gtaatggtac tgtagcagtg gcaaattctc attatgcagg accggcatat   120
tgtgtgggat attgtggcaa cagtggagtg gtgacaagaa atgccaatgc agatcttgca   180
agaactgcat ag                                                       192

<210> SEQ ID NO 30
<211> LENGTH: 194
<212> TYPE: DNA
<213> ORGANISM: Arthorbacter gandavensis

<400> SEQUENCE: 30
atgagcaata tcttagcagg aaagttacag acaggagcag actttgaagg cagcaaatgg    60
ggatgtgttt gtagtggaag cacagcagta gcaaactctc ataatgcagg accggcgtat   120
tgcgtaggat actgtggaaa caacggagta agtgactaga aatgctaatg caaatgtcgc   180
aaaaacggca ataa                                                     194

<210> SEQ ID NO 31
<211> LENGTH: 192
<212> TYPE: DNA
<213> ORGANISM: Arthorbacter gandavensis

<400> SEQUENCE: 31
atgagaaaaa tcgtagcagg aaagttacag acaggagcag actttgaagg cagcagaagt    60
ggatgtgttt gtagtgcaag cgcagcagta gcaagctctc attatgcagg accagcatat   120
tgcgtaggat actgtggaaa ccgtggagca gtaacgagaa atgcgaatta taatcttgca   180
aaaaaaaact ag                                                       192

<210> SEQ ID NO 32
<211> LENGTH: 192
<212> TYPE: DNA
<213> ORGANISM: Arthorbacter gandavensis

<400> SEQUENCE: 32
atgaaattag tagaaacaaa aacaacaaaa acaggaacag actttgaagg aaatagggct    60
ggatgtattt gtaatggtac tgtagcagtg gcaaattctc attatgcagg accggcatat   120
tgtgtgggat attgtggcaa cagtggagtg gtgacaagaa atgccaatgc agatcttgca   180
agaactgcat ag                                                       192

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
tggggatgtg tttgtagtag                                                20

<210> SEQ ID NO 34
<211> LENGTH: 20
<212> TYPE: DNA
<213> ORGANISM: Artificial Sequence
```

<220> FEATURE:
<223> OTHER INFORMATION: Primer

<400> SEQUENCE: 34
tccgtttttg cgacatttgc                                               20

<210> SEQ ID NO 35
<211> LENGTH: 30
<212> TYPE: DNA
<213> ORGANISM: Artificial Sequence
<220> FEATURE:
<223> OTHER INFORMATION: Primer

<400> SEQUENCE: 35
atgaatgctg ggcgagaaat ttgtgcggac                                    30

<210> SEQ ID NO 36
<211> LENGTH: 30
<212> TYPE: DNA
<213> ORGANISM: Artificial Sequence
<220> FEATURE:
<223> OTHER INFORMATION: Primer

<400> SEQUENCE: 36
ggagaccgca cctactggac aatctccttc                                    30

<210> SEQ ID NO 37
<211> LENGTH: 22
<212> TYPE: DNA
<213> ORGANISM: Artificial Sequence
<220> FEATURE:
<223> OTHER INFORMATION: Primer

<400> SEQUENCE: 37
gaaaggagga acaaaacatg ag                                            22

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
tcgtgccaga ttagcatttg                                               20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
agagtttgat cctggctgag                                               20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
aaggaggtga tccagccgca                                               20